(12) United States Patent
Bastian

(10) Patent No.: US 12,306,186 B1
(45) Date of Patent: May 20, 2025

(54) LIVE TESTS FOR DIAGNOSIS OF TRANSMISSIBLE SPONGIFORM ENCEPHALOPATHY IN ANIMALS AND HUMANS

(71) Applicant: Frank O. Bastian, New Orleans, LA (US)

(72) Inventor: Frank O. Bastian, New Orleans, LA (US)

( * ) Notice: Subject to any disclaimer, the term of this patent is extended or adjusted under 35 U.S.C. 154(b) by 0 days.

(21) Appl. No.: 18/787,340

(22) Filed: Jul. 29, 2024

Related U.S. Application Data

(63) Continuation-in-part of application No. 18/511,526, filed on Nov. 16, 2023, now abandoned, which is a continuation-in-part of application No. 17/017,439, filed on Sep. 10, 2020, now abandoned.

(60) Provisional application No. 62/898,378, filed on Sep. 10, 2019.

(51) Int. Cl.
| | |
|---|---|
| *G01N 33/53* | (2006.01) |
| *A61K 39/02* | (2006.01) |
| *C07K 14/195* | (2006.01) |
| *G01N 33/569* | (2006.01) |

(52) U.S. Cl.
CPC .... *G01N 33/56911* (2013.01); *A61K 39/0208* (2013.01); *C07K 14/195* (2013.01); *G01N 2469/10* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 6,033,858 A * | 3/2000 | Bastian | C12Q 1/689 435/6.15 |
| 7,888,039 B2 * | 2/2011 | Bastian | G01N 33/6896 435/7.1 |

* cited by examiner

*Primary Examiner* — Jennifer E Graser
(74) *Attorney, Agent, or Firm* — Garvey, Smith & Nehrbass, Patent Attorneys, L.L.C.; Seth M. Nerhbass; Fabian M. Nehrbass

(57) ABSTRACT

We identified a novel spiralin protein on the membrane of a *Spiroplasma* sp. isolated from CWD infected deer to which we have made recombinant protein that immune reacts with sera from CWD infected deer and not with controls. This recombinant spiralin protein is being developed into live diagnostic tests for CWD including ELISA and lateral flow assays which are also applicable for diagnosis of scrapie in sheep and Creutzfeldt-jakob disease (CJD) in humans. Monoclonal antibodies developed against the recombinant spiralin protein will be used to identify the microbe in formalin fixed tissues by immune histochemistry. Identification of the entire spiralin gene for this CWD associated *Spiroplasma* is ongoing using real time PCR since we have the genomic RNA sequence of this microbe and PCR primers from past experiments that are effective in identifying CWD cases. The recombinant novel spiralin protein is being tested as a preventative vaccine.

14 Claims, 8 Drawing Sheets
Specification includes a Sequence Listing.

LIVE TESTS FOR DIAGNOSIS OF TRANSMISSIBLE SPONGIFORM ENCEPHALOPATHY IN ANIMALS AND HUMANS

CROSS-REFERENCE TO RELATED APPLICATIONS

This is a continuation in part of U.S. patent application Ser. No. 18/511,526, filed 16 Nov. 2023, which is a continuation in part of U.S. patent application Ser. No. 17/017,439, filed 10 Sep. 2020, which claims benefit of U.S. Provisional Patent Application Ser. No. 62/898,378, filed 10 Sep. 2019, each of which is hereby incorporated herein by reference.

STATEMENT REGARDING FEDERALLY SPONSORED RESEARCH OR DEVELOPMENT

Not applicable

NAMES OF PARTIES TO JOINT RESEARCH AGREEMENT

Not applicable

INCORPORATION-BY-REFERENCE OF MATERIAL

The sequence listing submitted herewith (SEQ ID 1) is incorporated by reference as if copied herein in extenso. The sequence listing submitted is found in the XML file titled 3-Recombinant Spiralin Protein Sequence.xml; the sequence listing was created on 24 Jul. 2024; the file is 1,976 bytes.

BACKGROUND OF THE INVENTION

1. Field of the Invention

The invention is based on the discovery of a novel spiralin protein from the membrane surface of a *Spiroplasma* species yet unknown that is consistently isolated from brain and lymph node tissues from chronic wasting disease (CWD) infected deer as well as from other transmissible spongiform encephalopathies (TSE) including scrapie in sheep and Creutzfeldt Jakob disease (CJD) in humans. The discovery involved use of 2D Gel Electrophoresis of the fragmented *Spiroplasma* CWD isolate pellet from cell-free culture followed by Western blot using sera from CWD-infected deer and sera from normal control deer. The result was visualization of a single protein dot that immune reacted with the CWD positive sera and not with control sera. The protein dot was excised from the gel and sequenced using mass spectrometry. Recombinant protein was made to that immunoreactive protein sequence and was also shown to immune react to the CWD positive deer sera and not to control deer sera. This novel spiralin protein showed only 12% homology to spiralins of other *Spiroplasma* species. Therefore this recombinant novel spiralin protein from the membrane surface of the *Spiroplasma* species considered to be the causal agent of the TSEs is applicable for development of live tests for CWD and other TSEs including 1) lateral flow and 2) ELISA (Enzyme-Linked Immunoassay). These tests are applicable to detect presence of the *Spiroplasma* infection from body fluids obtained from animals susceptible to TSEs including sera from dementia patients suspect of having CJD. Aqueous fluid from the eye of deer or other animals susceptible to CWD contain antibodies that will immune react with the CWD positive sera. These tests have application for live diagnosis of scrapie-affected sheep and Creutzfeldt-Jakob disease (CJD) in humans and is based upon a prior patent of inventor (U.S. Pat. No. 7,888,039, Feb. 15, 2011, incorporated by reference). The novel *Spiroplasma* spiralin membrane recombinant protein used for development of these live diagnostic tests for CWD has application for acting as a preventative vaccine. Monoclonal antibodies made against the novel recombinant spiralin protein will be used for immune identification of the microbe in tissues from deer infected with CWD and in human tissues infected with CJD, therein providing a diagnostic tool for formalin-fixed tissues. These tests potentially will be able to detect new strains of *Spiroplasma* involved in the TSEs and may be applicable for identification of the source of the TSE infection.

Transmissible spongiform encephalopathies (TSE) are fatal infectious encephalopathies of man and animals. Although considered rare, Creutzfeldt-Jakob disease (CJD) in humans affects patients ranging from as young as 5 years to elderly patients. It is noteworthy that many teenagers died during the mad cow pandemic from variant form of CJD; those dead would likely have survived with administration of monoclonal antibodies against the bacterial membrane novel spiralin protein as a form of immunotherapy. CJD afflicted patients are difficult to diagnose clinically and show rapid neurological decline with death within a few months. Often, CJD is confused with other forms of dementia such as Alzheimer's disease (AD), Parkinson's disease and may be part of the AD complex in 13% of cases as shown by observation of prion protein in a tissue review. Diagnosis currently involves invasive procedures such as brain biopsy for detection of misfolded prion protein. There is a potential problem with contamination of instruments used in the brain biopsy representing a danger by use in subsequent patients, which we now know is due to bacterial biofilm formation which is essentially impossible to remove. Therefore, diagnosis by serological test such as a lateral flow test would avoid this danger. Furthermore, serological testing may give us the full spectrum of the disease since pathological changes and prion amyloid deposition are late disease changes. The same disease was well known in the animal world as the mad cow disease epizootic in cattle which was passaged to humans. Kuru was a TSE in a cannibalistic tribe and scrapie has been known for over 300 years in sheep. TSE is currently causing the panzootic of chronic wasting disease (CWD) in cervids which is widespread in the United States, Canada, Europe and South Korea. Scrapie has been known for decades as TSE in sheep. Although mad cow disease has mostly died out, residual cases are seen in Britain and the remnants of disease is potentially a danger in the cattle industry. CWD is spreading widely in both captive and wild cervid populations therein producing a large environmental reservoir of the infectious agent for potential spread to humans as CJD.

2. Description of Related Art

Current diagnostic tools for identifying TSE in animals or humans are grossly inadequate and current tests used by the USDA to identify live cases of CWD-infected deer are based on the wrong science. Diagnosis is typically made by pathological examination of the brain or rectal lymphoid tissue (animals) showing deposits of misfolded protein amyloid referred to as prions. The problem is that while the presence of the misfolded prion is diagnostic of TSE, the idea that these rogue proteins are the cause of TSE rather than just a manifestation of the process has resulted in not looking for other possible causative agents or disease markers. As a result, all efforts are to identify prion amyloid which cannot be done serologically. The detection of the misfolded prion protein requires brain or rectal biopsy and in-lab staining methods that are often limited to more specialized laboratories.

A major problem in handling the current global CWD epizootic is the current lack of a workable live diagnostic test for TSEs. A disease-specific misfolded protein amyloid deposited in diseased tissues during the course of TSE infection serves as a surrogate marker for these diseases. The use of the quaking test where diseased tissues are mixed with recombinant normal prion isoform and subjected to sonication or severe shaking has proved unreliable with difficulty diagnosing 50% of CWD cases. These amyloid proteins referred to as prion (a term coined by Dr. Prusiner) have been unfortunately implicated in the pathogenesis of the TSEs as the causal agent rather than just a manifestation of the disease). Prions are derived from misfolding of a normal cell surface prion protein isoform, which has the identical amino acid sequence as the pathological prion amyloid protein. The prion is suspect to be the receptor protein for the Spiroplasma bacterium and the misfolding may be due to interaction of the normal prion isoform with Hsp60 on the surface of the bacterium which is a known protein folder. It is assumed in the quaking test that misfolded prion protein in the sample is causing the misfolded prion diagnostic of the disease without any supporting data. Remember that the inventor's laboratory can isolate the novel *Spiroplasma* from the CWD sample and the test could simply be picking up presence of the microbe in the sample which is the cause of misfolding when binding to the normal prion isoform. This is a very inefficient way of detecting presence of the novel *Spiroplasma* and the serological detection of the bacterium is much more efficient in making a diagnostic test. Thus, attempts to develop a diagnostic live test for prion amyloid derived from an altered self-protein have not been successful.

BRIEF SUMMARY OF THE INVENTION

The present invention relates generally to discovery of a novel membrane protein from the *Spiroplasma* bacterium consistently isolated from TSEs. Recombinant protein made from the sequence of this novel spiralin protein immune reacts with sera from CWD infected deer and not with sera from normal deer. This is a major breakthrough which allows for the development of serological live tests for CWD, CJD, and other TSEs, and it can also serve as the basis for development of preventive vaccines and possible immunotherapy for use in human CJD cases This present invention provides live diagnostic serological tests for TSEs including ELISA and lateral flow tests. Additionally, the recombinant spiralin protein acts as a recombinant vaccine and antibodies produced against the recombinant novel spiralin protein can be used in the future for immunotherapy for human CJD infection. Antibodies against the spiralin recombinant protein can be used to make variant forms of diagnostic serological tests and vaccine. Antibodies against the recombinant spiralin protein are applicable to developing diagnostic immunohistochemical tests for examining tissue paraffin sections from past cases.

The present invention provides an instant diagnostic test for TSE by detection of antibody response to a novel wall-less spiral bacterium (*Spiroplasma* sp.) that has been shown to be consistently associated with this infectious encephalopathy. Our laboratory has grown a wall-less bacterium in tissues from all forms of TSE in cell-free *Brucella* media and as subsurface colonies on agar plates using the same media formula. This huge breakthrough in the inventor's lab has provided abundant data showing the presence of this microbe consistently in TSE-affected tissues which has allowed us to identify surface proteins on the microbe membrane that serves as an analyte for development of live ELISA and lateral flow tests for CWD. These data provide the ability to create lateral flow and ELISA live diagnostic tests for these fatal encephalopathies.

The candidate protein antigens on the surface membrane of the novel *Spiroplasma* TSE isolate may also be used as markers of TSE infection and include a] heat shock protein as demonstrated in my prior patent (U.S. Pat. No. 7,888,039, Feb. 15, 2011); b] spiralin which ordinarily makes up 80% of the cell surface, and c] adhesin protein which is commonly used to make diagnostic tests for bacterial-related diseases. Heat shock protein (HSP60) associated with a bacterium is 100% common to a particular microbial species as opposed to showing only 70% homology with other microbial species. In my prior patent (U.S. Pat. No. 7,888,039, Feb. 15, 2011), I show the usefulness of this *Spiroplasma*-specific Hsp60 antigen in the ELISA format as a specific test for serological identification of CJD in humans and for identification of scrapie infection in sheep. In the present invention, we base our test on our discovery of the novel spiralin membrane protein and the recombinant protein and antibodies derived from that *Spiroplasma*-specific analyte. The ELISA test of the present invention, based on such technology, can be used for screening a large herd of deer while the instant lateral flow strip test of the present invention can be used by hunters to determine whether their kill is infected. The lateral flow test is also useful in diagnosing cases of CJD in humans and distinguishing the cases from AD. All of these applications are possible because of our discovery of a portion of the major surface membrane novel spiralin protein by two-dimensional (2D) gel electrophoresis wherein a single bacterial membrane protein immune reacted with CWD-specific antisera. That protein was excised from the gel and sequenced by Mass Spectrometry and revealed an absolutely novel spiralin protein with minimal homology (12%) to any other protein in the GenBank. We have the spiralin protein sequence in which the novel spiralin protein fragment is embedded which works as a diagnostic tool for diagnosis of CWD and other TSEs, but do not have the entire spiralin protein (gene) specific to the CWD *Spiroplasma* isolate. Work is continuing on determining the entire sequence of the spiralin gene for this microbe which is possible since we have the genomic RNA sequence of the CWD-associated *Spiroplasma*. Both the sequence of the recombinant protein that is being used to develop the serological tests for CWD and the other TSEs as well as the genomic RNA sequence of the microbe were identified.

Recombinant protein made from the sequence of the novel spiralin protein was shown to immune react with the CWD positive sera (FIG. 7) while controls were negative (FIG. 8). This breakthrough allows us the mechanism to make specific diagnostic tests for TSEs proposed in this application as well as a preventive vaccine.

The best prospect for strain identification is spiralin which makes up 80% of the cell surface of *Spiroplasma* sp. and immunological detection of spiralin protein variants is used to classify different strains of a *Spiroplasma* species. We have identified a portion of the sequence of the spiralin protein making up most of the surface membrane of the CWD-associated bacterium and we have an ongoing project to identify the entire spiralin gene using real time PCR and the genomic RNA of the microbe we have in our possession. We plan on using the full length spiralin protein sequence to make another recombinant protein to apply to further development of the live test. DNA sequence of the TSE bacterial isolate in different TSE cases will determine the varied *Spiroplasma* species involved. We have so far identified the complete genomic RNA sequence of the TSE *Spiroplasma* pathogen.

In the future we will also use similar methodology to identify adhesin protein specific for this novel *Spiroplasma* species and which is well known for development of diagnostic immunological tests.

Future studies will focus on identification of the DNA nucleic acid sequence of the novel *Spiroplasma* pathogen, which may be related to the Archaea because of the remarkable resistance of the organism to radiation, formalin, boiling, autoclaving, etc. We have already identified the genomic RNA sequence of the microbe which allows the strategy of using cDNA sequence to identify protein sequences of other immune candidate membrane proteins as antigens. Another option is to use polymerase chain reaction (PCR) to identify specific DNA sequences with which we have had considerable experience and success in linking the bacterium *Spiroplasma* to the TSEs. Since we have the microbe growing in cell-free culture, we will continue to try to identify the genomic DNA sequence of the microbe from which we can specifically identify the complete sequences of the various surface *Spiroplasma* membrane antigen candidates from the DNA genome of the organism.

The spiralin recombinant protein derived from the surface membrane of the CWD-associated *Spiroplasma* is currently being tested by samples of sera from CWD positive and normal deer sera. Once that test is deemed workable, we will test (ELISA) against a coded set of sera from a deer farmer. Once the method is validated with sera we will test against aqueous fluid from eyes obtained from CWD positive and negative deer. Once we determine that we can identify positive and negative animals by ELISA, we will test 30 plus eyes for reaction of antibodies in the aqueous to the recombinant spiralin protein from a series of unknowns supplied by the State wildlife veterinarian from Louisiana. It would be advantageous to make the diagnosis from eyes supplied by the hunter rather than expose the hunter to contamination trying to get brain tissue from an animal he has shot.

We propose that this novel spiralin antigen will be very specific for the *Spiroplasma* species involved in the TSEs since there is sparse homology with other *Spiroplasma* genomes therein showing that this TSE-related *Spiroplasma* species is novel. Using this methodology different strains of the pathogen may be identified in the future as involved in the pathogenesis of the TSEs. Recombinant spiralin protein has been made against the novel sequence of the TSE-related spiralin protein and showed positive immune reaction against sera from CWD positive deer and not to normal deer sera (FIG. 8). Once the test is validated by an ELISA study of sera from coded collection of positive and negative CWD affected deer, the protein will be incorporated as well into the lateral flow test along with *Spiroplasma* specific Hsp60 and other *Spiroplasma*-specific surface protein markers, when available as a complex lateral flow test.

The lateral flow method has application for testing instantly individual TSE cases without need of in-lab work or special preparation of the test sample. This feature is especially applicable in diagnosis of CJD in patients presenting with dementia deemed necessary since CJD is misdiagnosed clinically as Alzheimer's disease in 13% of cases. In one or more embodiments, the live lateral flow tests incorporate multiple *Spiroplasma*-specific surface antigens. The lateral flow test can be used by veterinarians who, for example, need to guarantee the health of an animal for shipping. The lateral flow instant test is especially applicable for hunters who need to know whether their kill is infectious before they dress the animal. On the other hand, the ELISA format has application using the novel spiralin antigen for testing herds of animals for TSE.

Thus, a live test is essential to handle this animal and human health problem, and this invention can be used to remove or decrease the animal reservoir of CWD infection for the prevention of human CJD infection.

The laboratory of the present inventor has been conducting research on the consistent presence of a novel *Spiroplasma* infection in TSE-affected tissues for over 40 years. *Spiroplasma* are tiny, motile, wall-less bacteria primarily known as pathogens in plant and insect diseases. The present inventor has shown by molecular and morphological studies evidence of a *Spiroplasma* sp. in scrapie, CWD and CJD-affected brain and lymphoid tissues. *Spiroplasma* have been seen by darkfield microscopy in aqueous fluid from anterior chamber of eyes of sheep with scrapie, suggesting that examination of the aqueous fluid from the eye of the animal using our lateral flow test may be applicable for instant diagnosis of CWD in the killed deer. In a recent breakthrough, the present inventor has been successful in culturing a novel *Spiroplasma* species from CJD, scrapie and CWD-affected brain and lymphoid tissues into cell-free special *Brucella* media that contains sodium bisulfite, a reducer, creating an environment of low oxygen tension, which appears to be conducive for growth of this novel bacterium. The novel bacterial isolate forms tiny subsurface colonies on special agar plates (prepared using *Brucella* media) that are characteristic of the subsurface colonies formed by *Spiroplasma* spp. The present inventor has used this colony assay method to show the TSE-*Spiroplasma* isolate survives various extreme physical and chemical treatment simulating the biologic properties of the transmissible agent/s of the TSEs. The TSE-*Spiroplasma* isolate survives standard liquid autoclave sterilization wherein the liquid load is heated to a temperature of 250° F. (121° C.) at a pressure of 15 psia above atmospheric pressure (roughly 29.6 psia). The TSE isolate survives boiling for one-hour, 10% formalin for 18 hours (usual concentration of fixative for preservation of tissues for pathogenic examination), extreme acidity below 2 and a usually lethal dose of gamma irradiation (20,000 gy). The extreme biological properties of this *Spiroplasma* TSE isolate are comparable to the Archaebacteria (a group of microorganisms similar in size to eubacteria but with markedly different biological properties). Examples of Archaea are those microbes associated with old faithful in Yellowstone Park. The present inventor's discovery of an extreme thermoacidophilic bacterium as the cause of TSE represents the first description of such a novel infection in mammals. The biologic properties of the TSE *Spiroplasma* isolate are identical to susceptibility studies of the transmissible TSE agent reported in the 1960s. These data had suggested that the causative pathogen of TSE was an unconventional organism and led to the theoretical idea of replicating proteins, which is in direct opposition to Pasteur's well-accepted germ theory.

The prion amyloid marker in TSE is a reaction product to the novel *Spiroplasma* infection related to interaction of the bacterium with the prion receptor protein on the host cell surface. The interaction of the bacterium with the prion receptor is complex in that bacterial specific markers such as heat shock protein on the bacterial surface are important for the attachment of the TSE *Spiroplasma* isolate to the normal prion isoform and in the process misfold the prion into its pathological misfolded protease-resistant form. This discovery has represented a major paradigm shift in understanding the pathogenesis of TSE and suggested a new investigative approach is necessary to develop a workable live diagnostic test for TSEs.

Our discovery that a novel *Spiroplasma* sp. causes TSE infection and that the normal cell surface prion protein serves as a receptor protein for the bacterium represented a significant step in designing a workable live diagnostic test for TSE. Supported by data reported by a Japanese research group that the normal prion isoform on the cell surface is a receptor for initiation of a bacterial infection, the present inventor proposes a model for initiation of TSE infection by a novel *Spiroplasma* sp., as seen in FIG. 1. In this model, the bacterium attaches to the prion protein receptor along with a complex of other specific bacterial markers, including bacterial surface glycoproteins and glycans. Also involved is *Spiroplasma*-specific heat shock protein (Hsp60) on the bacterial surface that is likely responsible for misfolding of the prion receptor after interaction with the bacterium creating the prion amyloid diagnostic marker of TSE disease. The bacterial-specific components interacting with the prion receptor protein are all candidate antigens which may be useful for developing a specific live immunological lateral flow test or ELISA for the diagnosis of TSE in a live human patient or animal.

It is noteworthy that CJD patients produce antibodies against *Spiroplasma*-specific Hsp60 (>95% of CJD cases) and not in age-matched controls (see ELISA data presented in prior patent). Sheep affected with scrapie also produce antibodies against *Spiroplasma*-specific Hsp60. The present inventor has patented use of *Spiroplasma*-specific Hsp60 as a diagnostic test for TSE (see U.S. Pat. No. 7,888,039). The use of *Spiroplasma*-specific Hsp60 is limited for this current application of the present invention since Hsp60 is common to all *Spiroplasma* species and therein not useful for separation from other *Spiroplasma* species or differentiating species of the causal agent. However, the detection of antibodies against *Spiroplasma*-related HSP60 in TSE infection is significant since TSE is highly suspect when the test is positive.

More significant is our discovery of a novel spiralin protein on the surface membrane of the TSE *Spiroplasma* isolate. Furthermore, the production of recombinant spiralin protein and the immune reaction of CWD related sera with that novel protein confirms that we now have the basis for a live diagnostic serologic test for the TSEs. The present inventor concludes that the striking finding that CJD patients and scrapie-affected sheep have circulating antibodies against a *Spiroplasma*-specific Hsp60 surface protein does have use in screening animals or CJD patients for TSE, but more importantly supports our discovery of a novel spiralin protein specific for the species of *Spiroplasma* involved in the pathogenesis of the TSEs. This major discovery represents supportive data for our rationale to develop an instant or substantially instant lateral flow diagnostic test for the TSEs based upon presence of *Spiroplasma*-specific antigens on the bacterial surface consistent with the novel microbe associated with the TSEs. Our premise is that the presence of circulating *Spiroplasma*-specific antibodies against those antigens in TSE-affected humans or animals is the basis for diagnosis of TSE.

The *Spiroplasma* TSE isolate induces infection by binding to the prion receptor infection. The interaction of the *Spiroplasma* pathogen with the prion receptor is dependent upon several *Spiroplasma*-specific components on the bacterial surface. The bacterium is covered with glycolipids and glycans that interact with the prion receptor. The glycans on the bacterial surface are substantially different from eukaryotic glycoproteins with regard to both composition and structure. They are unique for that bacterium and identifiable by induction of reacting antibodies. Thus, the specific glycan on the surface of the *Spiroplasma* TSE isolate represents a candidate specific marker of TSE infection that can be used to develop a variant of the lateral flow test.

Two infection-specific proteins on the *Spiroplasma* surface that are components of the bacterial cell wall are adhesin and spiralin. Spiralin variation occurs among different *Spiroplasma* species, which is used to categorize the *Spiroplasma* clade. Antibodies against the species-specific spiralin on the surface of the *Spiroplasma* TSE isolate can be used to identify this novel *Spiroplasma* species. The present inventor has sequenced RNA extracted from a pellet of the TSE *Spiroplasma* isolate that can be used to identify the complete spiralin and adhesin genes specific to this novel species of *Spiroplasma*. Antibodies prepared against recombinant proteins developed from sequences of those genes can be used in development of a variant of the lateral flow test. In addition, antibodies are produced against *Spiroplasma*-specific nucleic acids that can be used for development of a lateral flow diagnostic test. The infection-specific bacterial components, particularly Hsp 60 protein are shown to react on ELISA with antibodies present in sera from infected CJD and scrapie samples. In this application, we propose that specific antibodies, both polyclonal and monoclonal, produced against the novel spiralin membrane protein can be used for development of a variant of the lateral flow test of the present invention. These antibodies are applicable for developing preventive vaccines for protection of animal from TSE infection especially captive animals in deer farms or zoos, and for immune histochemical diagnosis of TSEs. Those antibodies are applicable for immune therapy for human CJD.

The present invention also provides for the development of a test from the preparation of antibodies against these specific *Spiroplasma* membrane antigenic markers are tested by Western blotting against lysates of the TSE *Spiroplasma* isolate. The antigens (the extracted specific *Spiroplasma* surface markers) are identified by reaction on Western blot against sera from CWD-affected deer for application for development of a diagnostic ELISA test. The optimum *Spiroplasma*-specific antibody and antigen preparations are used for development of two variations of the lateral flow test of the present invention, one to detect antibodies and the other to detect antigens. These products are submitted to a commercial entity for development of the ELISA and lateral flow tests that will be validated against *Spiroplasma* TSE lysates and the CWD related deer sera available in the lab. It is preference to develop the tests and vaccines using the recombinant form of the novel spiralin antigen discovered on the surface of the *Spiroplasma* sp. associated with CWD that reacts with sera from CWD infected deer since there is no possibility of inadvertent infection.

The present invention is critically important since there is an ongoing panzootic of CWD in deer, elk and moose in North America involving 30 states in the USA and three Canadian provinces as well as global outbreaks of CWD in South Korea and Norway. CWD poses a significant threat as an infection reservoir for human CJD. Hunters are particularly at risk. When a hunter kills a deer, elk or moose, he has no idea whether that animal is infected with CWD since the incubation period for CWD is 18 months, during which time the animal appears normal. Venison harvested from the kill is potentially infectious for human consumption. The experimental passage of CWD to monkeys has suggested CWD may be infectious to humans. CWD has been experimentally transmitted to cattle indicating the cattle industry is at risk thus producing another reservoir for human infection. The lateral flow test of the present invention will be particularly important to the hunter since an immediate positive live test for CWDs would lead him to abandon the kill for consumption and report the animal to the USDA as a positive.

The present disclosure describes development of an immune lateral flow test based upon the inventor's consistent success in growing the CWD *Spiroplasma* isolate in cell-free *Brucella* medium. Candidate infection-specific antigens are identified including 1) *Spiroplasma*-specific surface proteins, particularly spiralin and adhesin; 2) *Spiroplasma*-specific nucleic acids; 3) *Spiroplasma* surface glycans and/or glycoproteins that are specific for binding of the *Spiroplasma* organism to the prion receptor; and 4) *Spiroplasma*-specific Hsp60. These surface membrane bacterial antigens are extracted from pellets of the TSE *Spiroplasma* isolate currently grown in the lab using 2D gel electrophoresis and tested for cross-reactivity to sera from CWD-affected deer obtained from deer breeders and LA state wildlife veterinarian. Normal control deer sera are available from the Louisiana State Wildlife veterinarian. The novel spiralin membrane protein extracted from a TSE *Spiroplasma* isolate pellet has been partially sequenced and showed only 12% homology with known *Spiroplasma* species indicating the isolate is novel, suggesting that a diagnostic test based upon identification of surface proteins using that sequence is unique. The optimum *Spiroplasma*-specific antigens are identified and used to prepare ELISA and lateral flow tests commercially. The present inventor has shown that CJD patients produce significant immune reaction to *Spiroplasma*-specific recombinant Hsp60 protein (>95%) reported in the prior patent (U.S. Pat. No. 7,888, 039) of the present inventor.

Deer farmers, elk ranchers, cattle ranchers, and the like can use the novel lateral flow method of the present invention to identify live animals infected with TSE-associated *Spiroplasma* prior to onset of clinical signs and preemptively cull the infected animals from herds. The live testing of farmed deer using the present invention would remove the need for the USDA/WILD LIFE government agencies to decimate the herd due to lack of a workable live test.

The method of the present invention can also be used to diagnose living humans who have been infected with the TSE-associated *Spiroplasma* (e.g., Creutzfeldt-Jakob disease, CJD). It has previously been problematic to diagnose TSE (CJD) in living humans. Examination of cerebrospinal fluid using the standard 14-3-3 test has given equivocal results. The only definitive method of diagnosing TSE in humans until now has been by brain biopsy to show typical pathology of CJD, presence of prion protein by immune histochemistry or by similar postmortem analysis of brain tissue. The diagnosis of the disease serologically would provide the opportunity to treat the patient early in the disease process possibly by immune therapy using antibodies made against recombinant spiralin protein shown in this application. The serologic test would remove fears of contamination of histology laboratory equipment or neurosurgical instruments using current diagnostic procedures.

The method of the present invention can also be used to validate procedures used to sterilize equipment to render equipment noninfectious for TSEs. Without adequate methods to identify and diagnose the presence of TSE-associated pathogens, previous methods that are generally used to sterilize surgical equipment have often been ineffective, sometimes exposing subsequent patients to TSE infectivity with instruments that have been contaminated following use on a CJD patient.

A problem with prior diagnostic methods is that all of them have focused on deposition prion amyloid proteins in tissues, based on the hypothesis that prions were the causative agent. However, the prion protein can easily be separated from TSE infectivity and is absent in 10 percent of CJD cases. Data from the laboratory of the present inventor indicate that prion amyloid proteins are a tissue reaction product, or simply an infection specific marker, rather than a cause of disease; and that a novel *Spiroplasma* are actually the underlying cause of TSEs. Recent studies have shown that the normal prion isoform acts as a receptor protein for the *Spiroplasma* bacterium. The interaction of the bacterium (novel *Spiroplasma* sp.) with the normal prion isoform receptor presumably causes misfolding of the prion protein resulting in formation of the prion amyloid marker of TSE. The innovative method of the present invention allows one to focus on the actual etiologic agent, the disease-causing pathogen, rather than on a byproduct or marker (prion) of the disease.

The present invention includes an immune based lateral flow assay and an ELISA test that, for the first time, allows consistent detection of analytes (antibodies, antigens, nucleic acids, proteins) markers of a novel TSE-related *Spiroplasma* sp. in body fluids of animals and humans for purposes of diagnosing transmissible spongiform encephalopathy (TSE).

The ELISA is applicable for screening herds of animals (deer, cattle or sheep/goats) for infected animals. The lateral flow test (LFT) will be capable of detecting a positive animal/human infection instantaneously and best used on single case or small numbers of samples. These tests will use *Spiroplasma*-specific antigens (including the novel spiralin, adhesin or other *Spiroplasma*-specific surface membrane antigens that would be capable of identifying novel *Spiroplasma* species/strains) involved in the pathogenesis of CWD/CJD. The LFT would be practical for use on individual animals or cases of suspect CJD patients. The antigens would include Hsp60, the novel spiralin, adhesin (when available) and other *Spiroplasma*-specific antigens that may be identified in the future.

Utilizing ELISA and LFT tests together would provide all the information for tracing these infections in both animals and humans.

The tests would have application to hunters to identify CWD infection instantly in their kill. The preferred method, a simple lateral flow assay, can be used to diagnose chronic wasting disease (CWD) quickly or preferably instantly or substantially instantly in a newly killed deer, moose or elk or Creutzfeldt-Jakob disease (CJD) in a human patient presenting with recent onset dementia. This detection method has application for detection of the novel *Spiroplasma* sp. in tissue homogenate samples, body fluid samples, secretion and excretion samples or other samples from subjects suspected of being affected with transmissible spongiform encephalopathy (TSE). Monoclonal antibodies (4) have been produced against the recombinant spiralin protein produced from the spiralin fragment identified on the surface of the novel *Spiroplasma* involved in the pathogenesis of CWD and will be used to identify cases by immune histochemistry where formalin fixed tissues are only available for immune histochemistry.

The feasibility of development of the present invention has been the breakthrough research discovery of the present inventor that showed this novel *Spiroplasma* sp. can be isolated consistently from TSE-affected tissues in *Brucella* media that contains mild reducing agents (sulfite salts) that lower the oxygen tension. Culture of the novel *Spiroplasma* sp. in cell-free *Brucella* media allows production of monoclonal and polyclonal antibodies against surface epitopes of the bacterium that are applied for development of a lateral flow instant diagnostic test. This can be done by development of polyclonal antibodies or monoclonal antibodies against immune reactive proteins extracted from lysates of the bacterium but is safer and more reliable by the preparation of antibodies against the recombinant spiralin protein identified in this proposal. Also, nucleic acid extraction from a pellet of the *Spiroplasma* CWD isolate allows sequencing, genetic identification of surface membrane proteins on the organism, production of recombinant *Spiroplasma*-specific surface proteins and development of monoclonal antibodies to those proteins that can be used in development of the present invention. The novel method of the present invention potentially allows identification of different strains of TSE-associated *Spiroplasma* sp. Such information can be used to determine sources of TSE infection—e.g., from an environmental sources such as plants (grasses) or insects, contact with another TSE-infected animal or human, or contact with contaminated surgical instruments used on a CJD patient—allowing ability to trace infections to a source and to conduct epidemiological studies.

The present invention includes a method of detection of transmissible spongiform encephalopathy-associated *Spiroplasma*, the method comprising an ELISA for screening large populations (herds) of animals for infection by this novel *Spiroplasma* bacterium by inoculating a lateral flow device with a sample that contains disease-specific analytes as shown by ELISA or that is suspected to contain transmissible spongiform encephalopathy-associated *Spiroplasma*, antigens or specific antibodies against *Spiroplasma* specific antigens.

In one or more preferred embodiments, an analyte in the lateral flow device is preferably a monoclonal or polyclonal antibody specific for surface epitopes of the *Spiroplasma* sp. isolated from TSE-affected tissues. This would have application for identifying formalin fixed tissues.

In one or more embodiments, an analyte in the lateral flow device is recombinant *Spiroplasma* Hsp60 protein developed in prior issued patent #U.S. Pat. No. 7,888,039 B2 where the strategy is that *Spiroplasma* Hsp60 will identify all *Spiroplasma* infection. However, the identification of the novel *Spiroplasma* membrane marker is the preferred method.

In one or more preferred embodiments, an analyte in the lateral flow device is preferably a polyclonal antibody specific for surface epitopes of the *Spiroplasma* sp. TSE isolate.

In one or more preferred embodiments, an analyte in the lateral flow device is preferably a monoclonal antibody specific for surface epitopes of the *Spiroplasma* sp. TSE isolate.

In one or more preferred embodiments, an analyte is preferably a nucleic acid extracted from pellets of the cultured novel *Spiroplasma* TSE isolate.

In one or more preferred embodiments, the lateral flow device is preferably a direct immune assay.

In one or more preferred embodiments, the lateral flow device is preferably an indirect immune assay.

In one or more preferred embodiments, the lateral flow device is preferably a competitive immune assay.

In one or more preferred embodiments, diagnosing TSE infection in a mammal is preferably by obtaining a sample from a tissue, bodily fluid, or excreta from the mammal for detection of *Spiroplasma* by a method of the present invention.

In one or more preferred embodiments, the tissue and/or body fluid sample is preferably selected from the group consisting of brain tissue, spinal cord, dura mater, corneal tissue, lymph node tissue, tonsil tissue, rectal tissue, feces, urine, cerebrospinal fluid, aqueous fluid from the eye, vitreous fluid from the eye, spermatozoa, semen, milk, and blood.

In one or more preferred embodiments, the mammal is preferably a sheep, goat, deer, elk, or cow; and wherein the clinical signs preferably comprise one or more of the following: ataxia, bruxism, neurological deterioration, wasting, and disorientation.

In one or more preferred embodiments, the mammal is preferably a human; and wherein the clinical signs preferably comprise rapidly progressing dementia, ataxia, or myoclonus.

In one or more preferred embodiments, the sample is preferably a wash collected from the surface of a sonicated medical instrument or veterinary instrument.

In one or more preferred embodiments, the sample is preferably collected from a plant, an insect, soil, or another environmental source that contains or that is suspected to contain transmissible spongiform encephalopathy-associated *Spiroplasma*.

In one or more preferred embodiments, the mammal is preferably a member of a domesticated or semi-domesticated herd; and wherein a method of the present invention preferably comprises the step of culling the mammal from the herd if the diagnosis is positive for *Spiroplasma* infection in the mammal.

In one or more preferred embodiments, a method of the present invention preferably comprises the step of shipping the animal TSE-free to a new location as determined if the diagnosis is negative for *Spiroplasma* infection as determined by the lateral flow device therein declaring the animal is free of CWD.

In one or more preferred embodiments, the sample is preferably collected from blood, brain, spinal cord, or aqueous fluid from the eyes from killed wild game; and wherein a positive result for the presence of *Spiroplasma* indicates that the meat is unsafe to consume; and wherein a negative result indicates that the meat is not a potential source of CWD *Spiroplasma* infection.

The present invention includes a method of making the lateral flow device as described in this application.

In one or more preferred embodiments, the present invention includes a useful test result that preferably occurs in less than 1 hour (essentially instantly).

In one or more preferred embodiments, the present invention includes a useful test result that preferably occurs in less than 30 minutes.

In one or more preferred embodiments, the present invention includes a useful test result that preferably occurs in less than 15 minutes.

In one or more preferred embodiments, the present invention includes a useful test result that preferably occurs in less than 2 minutes.

In one or more preferred embodiments, the present invention includes a useful test result that preferably occurs in less than 1 minute.

In one or more preferred embodiments, the present invention includes a useful test result that preferably occurs in less than 30 seconds.

In one or more preferred embodiments, the present invention includes a useful test result that preferably occurs in less than 15 seconds.

In one or more preferred embodiments, the present invention includes a useful test result that preferably occurs substantially instantly.

In one or more preferred embodiments, the present invention includes a useful test result that preferably occurs instantly.

The present invention includes use of the ELISA/LFT tests based upon the *Spiroplasma* specific recombinant novel spiralin protein identified in the novel *Spiroplasma* TSE isolated. The development of these immune based serological tests for diagnosis of TSE in live animals/humans is possible because of our ability to consistently grow the novel TSE *Spiroplasma* isolate in cell-free *Brucella* medium and as colonies on agar made with *Brucella* medium. The organism has been extracted from filtrates obtained from homogenized CWD-affected deer tissues (brain and/or lymphoid tissues). The extracted bacteria are grown in cell-free media incubated at 35 degrees Celsius for one to two weeks. The isolate forms typical subsurface colonies on agar prepared with special *Brucella* medium. The broth culture is centrifuged and the pellet collected then washed with phosphate buffer saline (PBS). The washed pellet is disrupted by freeze thawing (placing in −80 degrees C. freezer overnight then fragmented by sonication).

The microbe plus CWD positive deer sera were used to identify a portion of the spiralin surface protein from the microbe and discover the sequence which was used to make recombinant spiralin protein applicable for development of an ELISA and lateral flow test. The manufactured ELISA plates and LFT device can then be tested against blood samples from CWD-affected deer as well as control normal deer. The device can then be validated in a mouse model of CWD. The test device can be subjected to field testing.

The present invention is based on the success of developing an ELISA test for detection of the *Spiroplasma* infection responsible for CWD. The present inventor has consistently isolated a novel *Spiroplasma* sp. from chronic wasting disease (CWD)-affected deer tissues which has been essential to identify a more specific surface antigen (spiralin) for this causal agent of CWD. The present inventor has been able to grow the CWD-isolate in vitro, and thus is able to prepare antibodies against surface epitopes. However, the preferred method is the current invention wherein a novel spiralin protein that reacted with CWD sera was identified and recombinant protein made from sequence of that protein also immune reacted with sera from CWD infected animals and not from controls therein providing the opportunity to prepare live diagnostic serological tests for CWD infected animals and CJD patients. These accomplishments can now be applied to preparing a hunter handheld instant or substantially instant lateral flow immunological test (LFT) to identify CWD infection in the deer he has just killed to determine whether the meat is safe for consumption. The tests will be prepared commercially. Monoclonal and polyclonal antibodies against specific immune reactive proteins on the membrane surface of the organism can be used to make these tests very specific and can be used to identify specific strains of the pathogen and thus trace infections. These antibodies can be used to prepare a preventative vaccine. Widespread use of such a test can produce accurate surveillance data to document the epidemiology of CWD infection in nature and can be used to trace sources of CWD infection. The LFIT preferably has application to diagnosing Creutzfeldt-Jakob disease (CJD) in humans where at present there is no workable diagnostic test other than brain biopsy, and potentially determine if there is a link of the strain of *Spiroplasma* sp. identified in CJD to a CWD-affected animal source.

BRIEF DESCRIPTION OF DRAWINGS

For a further understanding of the nature, objects, and advantages of the present invention, reference should be made to the following detailed description, read in conjunction with the following drawings, wherein like reference numerals denote like elements and wherein.

DETAILED DESCRIPTION OF THE INVENTION

Figure 1:
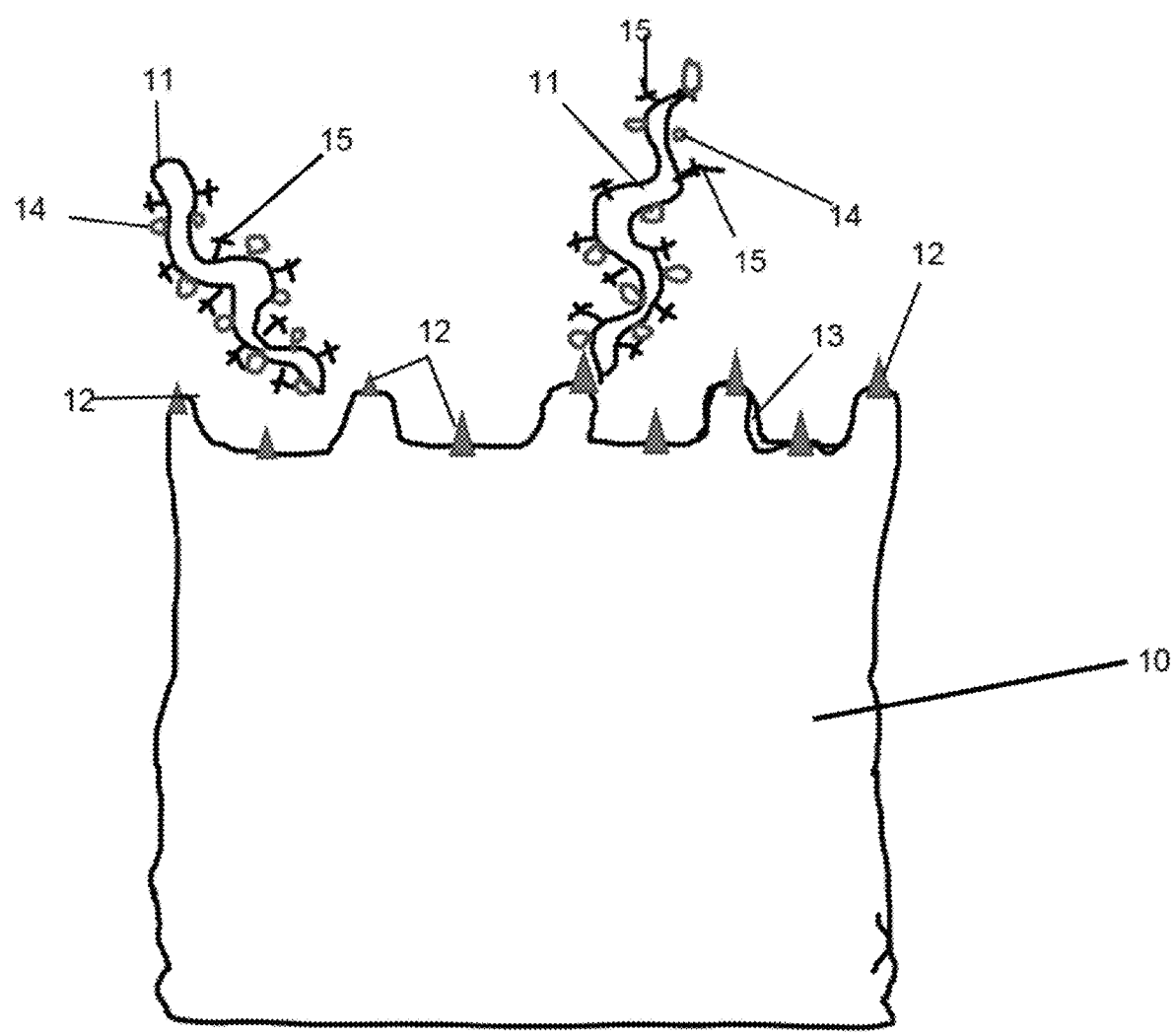
FIG. 1 is a view of a proposed infection model for TSE infection. This model supports the accuracy and efficiency of a preferred embodiment of the present invention targeting infection-specific bacterial components.

A novel *Spiroplasma* sp. was isolated from brain and lymphoid tissues affected with scrapie, CWD and CJD in *Brucella* special media, showing a requirement for low oxygen tension. The TSE isolates grew on Bacto Schaedler agar plates forming distinctive *Spiroplasma* colonies. The *Spiroplasma* was also isolated from archived sheep and goat brain and lymph nodes from animals experimentally inoculated with TSE *Spiroplasma* isolates therein fulfilling Koch's postulates of causality. The novel *Spiroplasma* grew to high titer in the cell-free media and pellets could be used to develop antibodies against surface epitopes. From this, one can develop monoclonal and polyclonal antibodies to use in the present invention, which includes a lateral flow assay developed to specifically identify the presence of the novel *Spiroplasma* isolate in body fluids from test animals or human dementia patients. Our approach was to identify surface proteins on the novel *Spiroplasma* TSE isolate then make recombinant protein to use in preparation of a diagnostic ELISA and LFT for diagnosis of TSE infection.

There are several different embodiments of the lateral flow test of the present invention where the target is antibody against TSE *Spiroplasma*-specific surface antigens or the antigen itself including 1) *Spiroplasma*-specific membrane proteins (spiralin and adhesin); 2) *Spiroplasma*-specific heat shock protein or glycans; and 3) nucleic acids related to the novel TSE *Spiroplasma* isolate. The antibody can be polyclonal (against whole surface bacterial proteins and/or glycans), monoclonal (against specific *Spiroplasma* surface proteins or peptides extracted from the *Spiroplasmas*) or monoclonal against recombinant proteins developed from sequences available from extracted *Spiroplasma* nucleic acids. The assay can be applied to blood, sera, urine, saliva and/or feces. The aqueous humor of the eye anterior chamber is particularly applicable. A positive result indicates that the test animal/human has TSE. Preferably, reading of the test is simple without needed training. Preferably, the test kit is stable and does not require refrigeration so it can be used out in the field, such as by a hunter to test whether the deer he just shot is infected with CWD.

*Spiroplasma* pathogen 11 has been shown by studies to interact with prion receptor 12 on cell surface 13. Candidate infection-specific antigens have been identified particularly spiralin and heat shock protein. Other analytes include 1) adhesin; 2) *Spiroplasma*-specific nucleic acids; 3) *Spiroplasma* surface glycans 15 and/or glycoproteins that are specific for binding of the *Spiroplasma* organism 11 to the prion receptor 12.

The present inventor has projected, based upon the Japanese studies [6] that the TSE *Spiroplasma* isolate bacterium 11 attaches to the prion protein receptor 12 along with a complex of other specific bacterial markers, including bacterial surface glycoproteins and glycans 15. Also involved is *Spiroplasma*-specific heat shock protein (Hsp60) 14 on the bacterial surface to which CJD patients form antibodies [7]. The *Spiroplasma*-specific Hsp60 protein is likely responsible for misfolding of the prion receptor 12 after interaction with the bacterium 11 likely due to the presence of the *Spiroplasma* specific heat shock protein 20 creating the prion amyloid diagnostic marker of TSE disease. The glycans 15 on the bacterial surface are substantially different from eukaryotic glycoproteins.

The fortuitous discovery of TSE-associated *Spiroplasma* growth in cell-free *Brucella* broth indicated that the reducing agent, sodium bisulfite, enhanced the CWD *Spiroplasma* isolate growth by lowering oxygen tension. The TSE-associated *Spiroplasma* is consistently and easily isolated from CWD-affected tissues into cell-free *Brucella* media allowing the present inventor to identify a novel spiralin protein analyte on the membrane surface of the microbe to which recombinant protein was made. The key to this success was the use of 2D gel electrophoresis followed by Western blot wherein a single protein immune reacted with sera from CWD positive deer and not with sera from normal deer. It is noteworthy that both the single protein identified by 2D gels and the recombinant form of that protein immune reacted to CWD positive sera indicating the basis for development of the ELISA and lateral flow serological tests. Since the novel *Spiroplasma* grew in cell-free broth culture it is possible to develop polyclonal and monoclonal antibodies to the surface proteins of the organism. However, there is a possibility of inducing infection by this latter method so it is much preferred to use the recombinant spiralin protein for development of the present invention. Similarly, polyclonal and/or monoclonal *Spiroplasma*-specific antibodies against the TSE *Spiroplasma* isolate can be induced and used in development of our invention. As shown in my prior patent, recombinant Hsp60 *Spiroplasma* specific protein has been used to produce an ELISA screening test but the methodology described in this application is a preferred and simplistic method.

The live tests described here can be used to remove CWD positive animals and thus the reservoir of CJD infection.

The TSE-associated *Spiroplasma* are "microaerophilic," bacteria that require oxygen but grow best under low oxygen levels. Typical oxygen levels for growth of microaerophiles is 2-10%, compared to normal atmospheric oxygen concentration of about 21%. For growth of the TSE-associated *Spiroplasma*, require oxygen for growth, but at low oxygen tension levels as shown by their preference for special *Brucella* media. *Spiroplasma* spp. will not grow under strict anaerobic conditions.

The recent discovery of the present inventor that the CWD *Spiroplasma* isolate is an extreme thermoacidophilic bacterium is especially pertinent in that Archaea microbes, which possess comparable resistant biologic properties also flourish in the presence of sulfite salts, supporting the premise of the present inventor that the CWD *Spiroplasma* isolate is likely derived from the Archaea. These data show that the causative agent of the TSEs is this novel *Spiroplasma* sp. CWD-isolate is more likely the causative agent of TSE rather than a lifeless protein, as proposed in the prion protein concept. Therefore, the ability of the present inventor to grow the organism in cell-free media, to identify a novel surface spiralin protein that reacts with CWD positive sera and to produce polyclonal and monoclonal antibodies against recombinant spiralin protein that will serve as a preventive vaccine strongly support the present invention as being an important effective diagnostic tool for the TSEs.

The invention may be used simply to detect TSE in a mammal, including a human, a cow, a deer, an elk, or a sheep. The *Spiroplasma* responsible for TSE infection will be identified by finding specific antibodies or specific antigens in sera or other body fluids obtained from CWD-affected animals or CJD-affected humans. We have shown that there is no immune reactivity against lysates of the TSE *Spiroplasma* isolates by Western blot against hyperimmune sera against several species of *Spiroplasma* (unpublished observations). There is no immune reaction of specific antibodies for *Spiroplasma mirum* against the *Spiroplasma* TSE isolate in tissue culture infection.

Example 6. In one embodiment, the present invention (lateral flow test), when positive, can be confirmed by incubation of filtered blood or tissue sample in *Brucella*-type media or agar plates at 35° C. for 6 to 14 days. Following the incubation period, the inoculated *Brucella* media appears slightly turbid, and motile *Spiroplasma* can be readily seen by dark-field microscopy. The Bacto Schaedler Agar plates overlayed with filtered TSE samples develop subsurface colonies characteristic of *Spiroplasma* growth. *Spiroplasma* colonies and growth in cell-free media provides the ability to produce polyclonal and monoclonal antibodies that can be used to develop the lateral flow test described in our invention. Growth of the *Spiroplasma* TSE isolate from suspect samples can be a confirmation of the presence of the organism in those samples.

A positive lateral flow test can be confirmed by polymerase chain reaction (PCR) as primers specific for *Spiroplasma* produce a 170 base pair PCR product from preparations of the TSE *Spiroplasma* isolates. The PCR reaction is robust when done on a nucleic acid extract from a pellet of the *Spiroplasma* TSE isolate.

The method of the present invention can be used as a test for TSE in living humans and other mammals. Secretions, tissue samples, bodily fluids from infected sources will yield immune reaction in positive cases as shown on the lateral flow test. This new approach is a less complicated, more cost-effective solution to cultivation of TSE-*Spiroplasma* isolates. The findings are instant or substantially instant and the method of the present invention is superior to attempts to make a TSE test for a living mammal based on detecting prions, as it both is simpler to implement, and is based on detecting the actual pathogen rather than detecting a byproduct of the infection. The method of the present invention can also be used to identify and isolate potential TSE-causing *Spiroplasma* in the environment, for example, in insect, soil, and plant preparations simulating media used to grow the *Spiroplasma* isolate from CWD infected tissues. Also, the chemistry of the sieve tubes of grasses closely resemble *Brucella* media that support the growth of the *Spiroplasma* isolate from CWD infected tissues suggesting that grasses could be a reservoir of infection. Also, the ability of *Spiroplasma* to produce biofilm allows the microbe to live in upper soil levels thus being available to infecting cervid and other animals that eat a lot of soil.

The method of the present invention is simpler and cost effective in confirming the diagnosis of TSE currently done by live animal inoculation and waiting for development of clinical signs of disease in the test animal (140 days).

The method of the present invention is simpler and cost effective in determining the diagnosis of TSE currently being done by identifying prion protein by immunohistochemistry which is dependent on the observer and subject to weak equivocal staining.

The method of the present invention is simpler, more cost effective, and more accurate determining the diagnosis of TSE currently being done by exposing the sample to multiple rounds of sonication (PMCA test) or to vigorous shaking (Quaking test). These tests relate to increase in prion amyloid by self-assembly of the amyloid protein. It is noteworthy that these tests show increase in prion protein but show no increase in infectivity suggesting one has nothing to do with the other. Furthermore, the PMCA and Quaking tests are less than 50% accurate and subject to false positives. Furthermore, the assumption that the misfolding is due to presence of prion amyloid in the sample may be erroneous since we know the *Spiroplasma* bacterium is present in the sample and is likely responsible for a positive test.

*Spiroplasma* nucleic acid has been extracted from cultured pellets of the *Spiroplasma* TSE isolate using phenol/chloroform extraction. Polymerase chain reaction (PCR) amplification of DNA extracted from the culture pellet, using two common bacterial oligonucleotide 16s rDNA primer sets and using a *Spiroplasma*-specific primer set, produced appropriate PCR product banding, consistent with the presence of *Spiroplasma* in culture. Sequencing of the PCR products have confirmed the presence of *Spiroplasma*-related ribosomal DNA sequences in the pellet, albeit the sequence suggested it to be from a novel *Spiroplasma* species. No *Spiroplasma* DNA was extractable when normal sheep brain was incubated in *Brucella* media for 2 weeks, indicating lack of any propagating *Spiroplasma* pathogen in the control. The availability of nucleic acid related to the novel *Spiroplasma* TSE isolate provide for developing an embodiment of the present invention.

Centrifugation of *Spiroplasma* culture-pellet obtained. *Spiroplasma* following incubation can be centrifuged at 20,000 g with formation of a small pellet. The pellet is prepared for detection of epitopes on the surface of the organism.

Polyclonal antibody specific to proteins on bacterial surface—a preferred embodiment of the lateral flow test: the pellet is directly inoculated into goats for production of polyclonal antibodies against the whole organism. The bacterium will be killed prior to inoculation using sodium thiocyanate or SDS which has been shown to kill the organism. The present inventor has used this methodology in the past without loss of immunogenicity. The goats will be bled and the hyperimmune sera is frozen at −80 degrees C. The specificity of the antibody is checked by Western blotting and dot blotting.

Monoclonal antibody specific to proteins on bacterial surface—a preferred embodiment of the lateral flow test: the pellet is prepared as a lysate by freeze thaw method. The lysate preparation is electrophoresed on an agar gel and a Western blot is performed using sera from CWD-affected deer. The immune reacting protein is extracted from the gel and sent for monoclonal antibody formation. The clone ideal for developing the test of the present invention is determined by Western blots/dot blots using the bacterial lysate of the present invention.

Monoclonal antibody specific to proteins on bacterial surface using recombinant proteins—a preferred embodiment of the lateral flow test: The sequence of the pelletized *Spiroplasma* isolate has been sequenced and informatics studies will identify proteins on the bacterial surface unique to this organism. Recombinant proteins made from these sequences will be submitted for monoclonal antibody formation. The reaction of individual clones will be tested against the *Spiroplasma* lysate and the recombinant protein by Western blotting.

Preparation of lateral flow test: The present invention includes a diagnostic device (Lateral flow immunoassay (LFT)(FIG. 2) used to show the presence or absence of *Spiroplasma*-related immune biomarkers in human or animal body fluids, which can determine whether there has been exposure to this novel *Spiroplasma* sp. isolated consistently from TSE-affected tissues in the laboratory of the present inventor. The LFT preferably contains a control line to confirm the test is working properly, along with one or more target or test lines. LFTs are based on immunoassay technology using nitrocellulose membrane, colored nanoparticles (or labels), and specific antibodies. The sample is added and can flow along the test device passing through the conjugate pad into the nitrocellulose membrane and then onto the absorbent pad.

Figure 5:
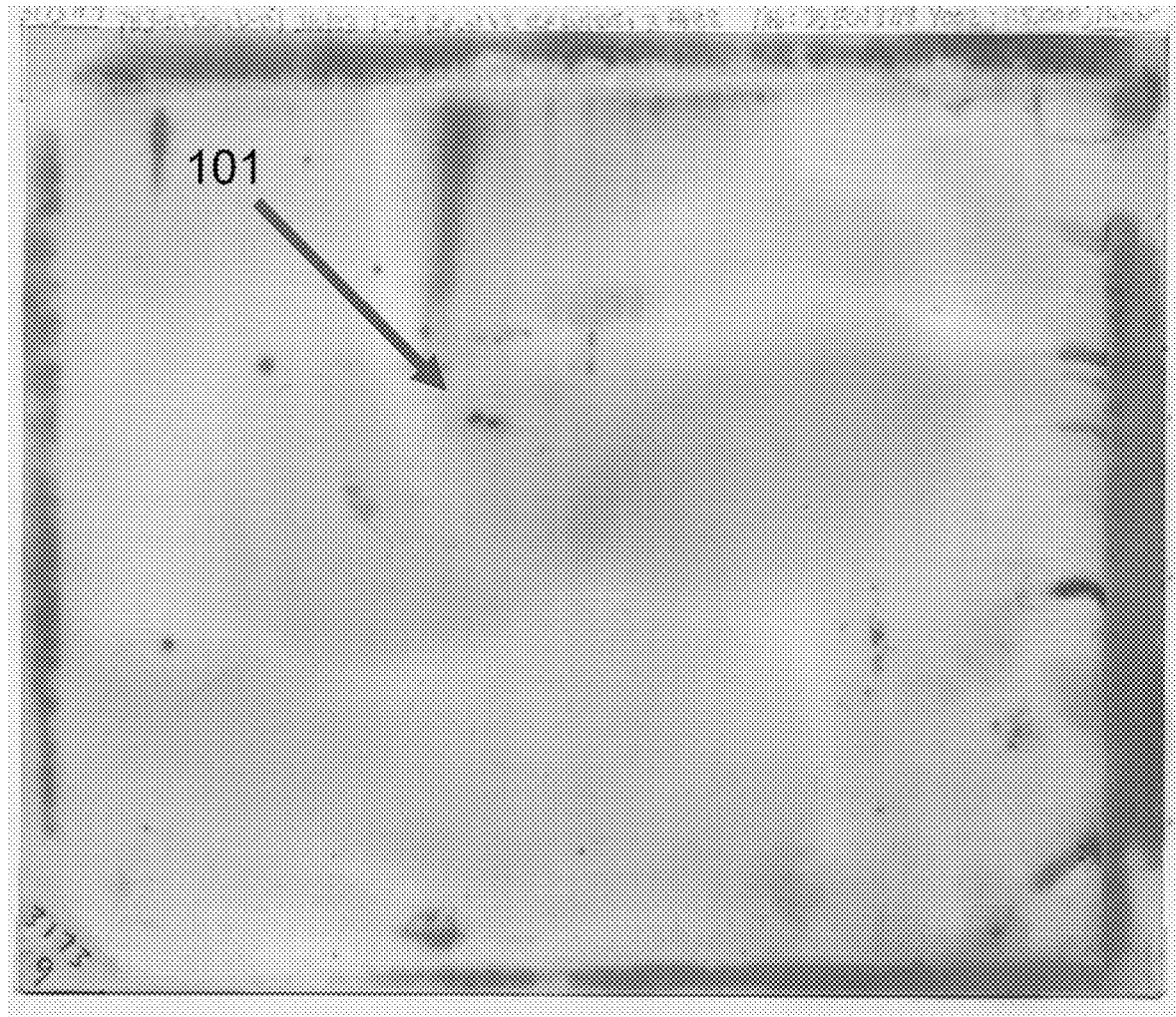
FIG. 5 a 2D gel electrophoresis showing the identification of a surface protein (spiralin) from novel *Spiroplasma* CWD isolate.

The LFT can work in the following way (FIG. 5).

The sample pad is the first stage of the absorption process.

The conjugate pad stores the conjugated labels and antibodies and will receive the sample. If the target is present, the immobilized conjugated antibodies and labels will bind to the target and continue to migrate along the test.

As the sample moves along the device the reagents situated on the nitrocellulose membrane will bind to the target at the test line. A colored line will form (the density of the line is quantitative depending on the amount of the target present). A rapid test can be combined with a reader to provide quantitative results.

The sample will pass through the nitrocellulose membrane into the absorbent pad. The absorbent pad will absorb the excess sample. The specification of the absorbent pad will have an impact on the volume of sample the test can incorporate.

Additional preferred embodiments of the lateral flow assay method:
1. Sandwich assays—A positive test is represented by the presence of a colored line at the test line position.
2. Competitive assays—A positive test is represented by the absence of a colored line at the test line position.
3. Lateral flow assays—Utilize conjugated gold, carbon, or colored latex nanoparticles within the conjugate pad. Other labels include magnetic beads or colored polystyrene beads. Regardless of the label types, they all create a three-way bond with antibodies and targets to make visible the control and test lines.

Lateral flow assays are preferably used in a dipstick format or in a housed cassette. The present invention requires minimal training to operate. Lateral flow assays of the present invention can be qualitative and read visually, or quantitative when combined with reader technology (see for example http://www.abingdonhealth.com/technology/).

There are several different embodiments of the test of the present invention where the target is antibody against TSE Spiroplasma-specific surface antigens or the antigen itself including 1) Spiroplasma-specific glycoproteins (spiralin and adhesin); 2) Spiroplasma-specific glycans; and 3) nucleic acids related to the novel TSE Spiroplasma isolate. The antibody can be polyclonal (against whole surface bacterial proteins and/or glycans, Spiroplasma surface proteins or peptides extracted from the Spiroplasmas) or monoclonal against recombinant proteins developed from sequences available from extracted Spiroplasma nucleic acids. The assay can be applied to cerebrospinal fluid, aqueous from an eye, blood, sera, urine, saliva and/or feces. A positive result indicates that the test animal/human has TSE. Preferably, reading of the test is simple without needed training. Preferably, the test kit is stable and does not require refrigeration so it can be used out in the field, such as by a hunter to test whether the deer he just shot is infected with CWD.

FIG. 1 shows a model for TSE infection, specifically by way of a cell 10 in contact with CWD Spiroplasma pathogen 11. As noted, Novel Spiroplasma TSE isolate surface proteins 11 is immunologically different from other Spiroplasma sp. Additionally, species-specific adhesin and spiralin proteins are found on bacterial surface. Spiroplasma pathogen 11 is implicated by prior studies to interact with prion receptor 12 (normal prion isoform receptor protein) on cell surface 13. Interaction with Hsp60 (a protein folder) forms prion amyloid marker. Candidate infection-specific antigens are identified in FIG. 1, including 1) Spiroplasma-specific surface proteins 11, particularly spiralin and adhesin; 2) Spiroplasma-specific nucleic acids; 3) Spiroplasma surface glycans 15 (chemically different from eukaryotic glycans) and/or glycoproteins that are specific for binding of the Spiroplasma organism 11 to the prion receptor 12; and 4) Spiroplasma-specific heat shock protein (Hsp60 on bacterial surface) 14.

The present inventor has projected, based upon the Japanese studies that the TSE Spiroplasma isolate bacterium 11 attaches to the prion protein receptor 12 along with a complex of other specific bacterial markers, including bacterial surface glycoproteins and glycans 15. Also involved is Spiroplasma-specific heat shock protein (Hsp60) 14 on the bacterial surface to which CJD patients form antibodies. The Spiroplasma-specific Hsp60 protein is likely responsible for misfolding of the prion receptor 12 after interaction with the bacterium 11 creating the prion amyloid diagnostic marker of TSE disease. The glycans 15 on the bacterial surface are substantially different from eukaryotic glycoproteins.

Figure 2:
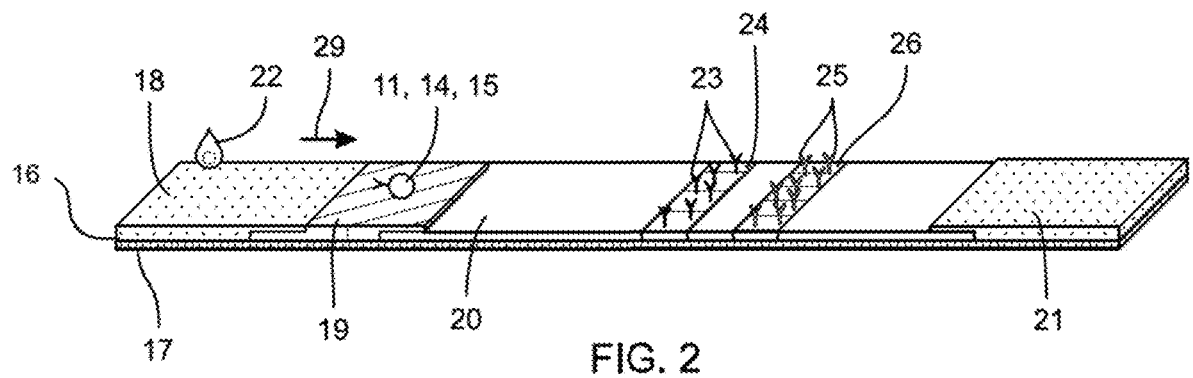
FIG. 2 shows a preferred embodiment of a lateral flow assay, rapid diagnostic test of the present invention.
Figure 3:
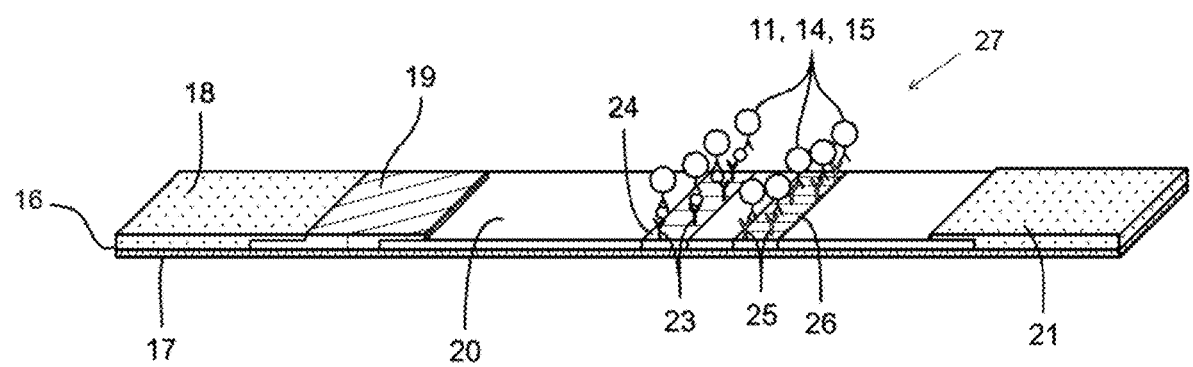
FIG. 3 shows a preferred embodiment of a lateral flow assay, rapid diagnostic test of the present invention with a positive result.
Figure 4:
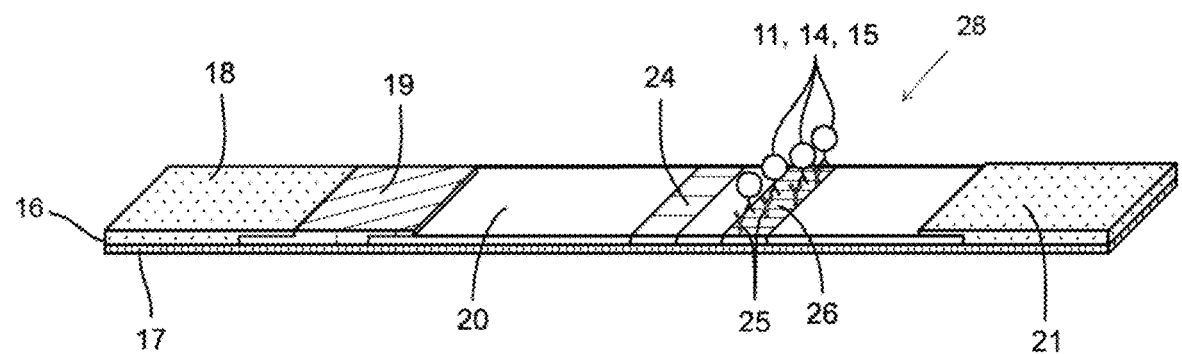
FIG. 4 shows a preferred embodiment of a lateral flow assay, rapid diagnostic test of the present invention with a negative result.

FIGS. 2-4 show a preferred embodiment of the rapid diagnostic test of the present invention. This preferred embodiment is a lateral flow assay test strip 16. The test strip 16 preferably has a backing 17. The backing 17 preferably has a membrane 20 on top, said membrane preferably having a sample zone 18, conjugation zone 19, and absorbent pad 21. Preferably, TSE specific particles such as Spiroplasma TSE isolate surface protein/Spiroplasma pathogen 11, Spiroplasma-specific heat shock protein/Hsp60 14, and/or Spiroplasma-specific glycans 15 are affixed to the membrane 20 in the conjugation zone 19. Preferably, a primary capture agent 23 is affixed to the membrane 20 in the test band 24. Preferably, a secondary capture agent 25 is affixed to the membrane 20 in the control band 26. Preferably, if a sample is sufficient in quantity and quality, it will activate the secondary capture agent 25 in the control band 26. A positive result 27 as shown in FIG. 3 occurs when antibodies in the sample 20 conjugate with TSE specific particles such as Spiroplasma TSE isolate surface protein/Spiroplasma pathogen 11, Spiroplasma-specific heat shock protein/Hsp60 14, and/or Spiroplasma-specific glycans 15 in the conjugation zone 19, and are captured by the primary capture agent 23 in the test band 24, and the sample 22 is sufficient in quantity and quality to activate the secondary capture agent 25 in the control band 26. A negative result 28, shown in FIG. 4 occurs when the sample 22 is sufficient in quantity and quality to activate the secondary capture agent 25 in the control band 26, but there is no antibody in the sample 22 to conjugate in the conjugation zone 19, thus, the primary capture agent 23 in the test band 24 is not activated.

Preferably, a sample 22 is applied to the sample zone 18 in an amount sufficient for obtaining accurate test results. For animals, a preferred sample 22 is aqueous fluid from the anterior chamber of the eye, preferably collected according to the procedure shown in FIG. 5 of my U.S. patent application Ser. No. 17/017,439 (filed 10 Sep. 2020), which is incorporated herein by reference. For human patients, the sample 22 is preferably cerebral spinal fluid collected according to known and approved medical procedures. After a certain period of time, preferably a few seconds to minutes, the sample 22 flows in the flow direction 29 across the membrane 20. Preferably, if the sample 22 contains antibodies specific to CWD, those antibodies will conjugate with the TSE specific particles such as Spiroplasma TSE isolate surface protein/Spiroplasma pathogen 11, Spiroplasma-specific heat shock protein/Hsp60 14, and/or Spiroplasma-specific glycans 15 that are affixed to the membrane 20 in the conjugation zone 19, thus indicating a positive result.

Sampling of the aqueous fluid from the eye is a preferred sampling that can be done in both live and postmortem animals. For example, when a hunter kills a deer, he/she should immediately sample the aqueous fluid from the eye prior to dressing the animal. If positive on a test of a preferred embodiment of the present invention, such as those shown in FIGS. 2-4, the animal should be left to the wildlife agency to dispose of. If a negative result is obtained, the animal can be dressed and the meat consumed. The testing can preferably involve both antigen and antibody testing, so two variations of the test kit can preferably be used.

The eyes, one frozen and one fixed in formalin, should be examined from any animal suspected to die of CWD. The eye is essentially involved in any form of TSE showing histologically a degenerative retinopathy. The corneal epithelia are infected as shown in experimental *Spiroplasma* infection in deer, which is supported by data showing the cornea to be infectious in scrapie and CJD to be passaged by corneal transplant. Using our ELISA or lateral flow tests described herein, a serological instant diagnosis can be made by examination of the aqueous fluid. Furthermore, the formalin fixed eye can be examined by immune histochemistry using prion antibodies as well as antibodies produced against the novel spiralin recombinant. This study is important in that if the tissues are diagnostic by histology and prion staining but negative for the spiralin, this result would indicate that there is evidence of a new strain of bacterial agent suggesting growing of the microbe from those tissues and characterizing the new infection as a new variant.

An antigen-based test is not shown in the drawings; however, it would be prepared similarly to the tests shown in FIGS. 2-4. Rather than antibodies in the sample 22 reacting in the conjugation zone 19, antigens in the sample 22 would react in the conjugation zone 19 causing a positive result.

This procedure can also be used by a deer farmer to test a sick animal as a live test. If an animal dies unexpectedly, sampling and testing should be done on the dead animal. Such testing should become widely used in zoos on both exotic ruminants and also on other susceptible species such as big cats, including lions and tigers, subhuman primates, and other animals.

In hospitals, testing should be done on any patient presenting with rapid onset dementia, also when a patient with dementia dies, postmortem testing should be done prior to autopsy, thus limiting exposure of medical personnel to CJD.

In the present invention, the isolation and identification of CWD related proteins from the surface membrane of the microbe was accomplished by use of two-dimensional electrophoresis (2D gel electrophoresis). Pellets of the novel *Spiroplasma* isolate grown to log phase in *Brucella* media along with sera from both CWD infected deer and normal control deer were sent to a laboratory. The *Spiroplasma* microbe was fragmented into individual proteins showing a starry sky appearance. The proteins showing up as individual dots was first separated according to isoelectric point and then those were separated in a perpendicular direction according to molecular weight. This was followed by a Western Blot using positive and negative sera which revealed a single dot doublet (see FIG. 5, arrow 101 pointing to single dot doublet) which was immune reactive to the CWD positive sera with no reaction with the control sera. The spot was cut out of the gel, sequenced using Mass Spectrometry and found to be a spiralin protein with no homology to any other protein. FIG. 5 shows the identification of a surface protein (spiralin) from novel *Spiroplasma* CWD Isolate by 2D Gel Electrophoresis. The protein 101 was cut out and sequenced by mass spectrometry.

The spiralin sequence was obtained from novel *Spiroplasma* cultured from CWD-affected deer tissues.

Figure 7:
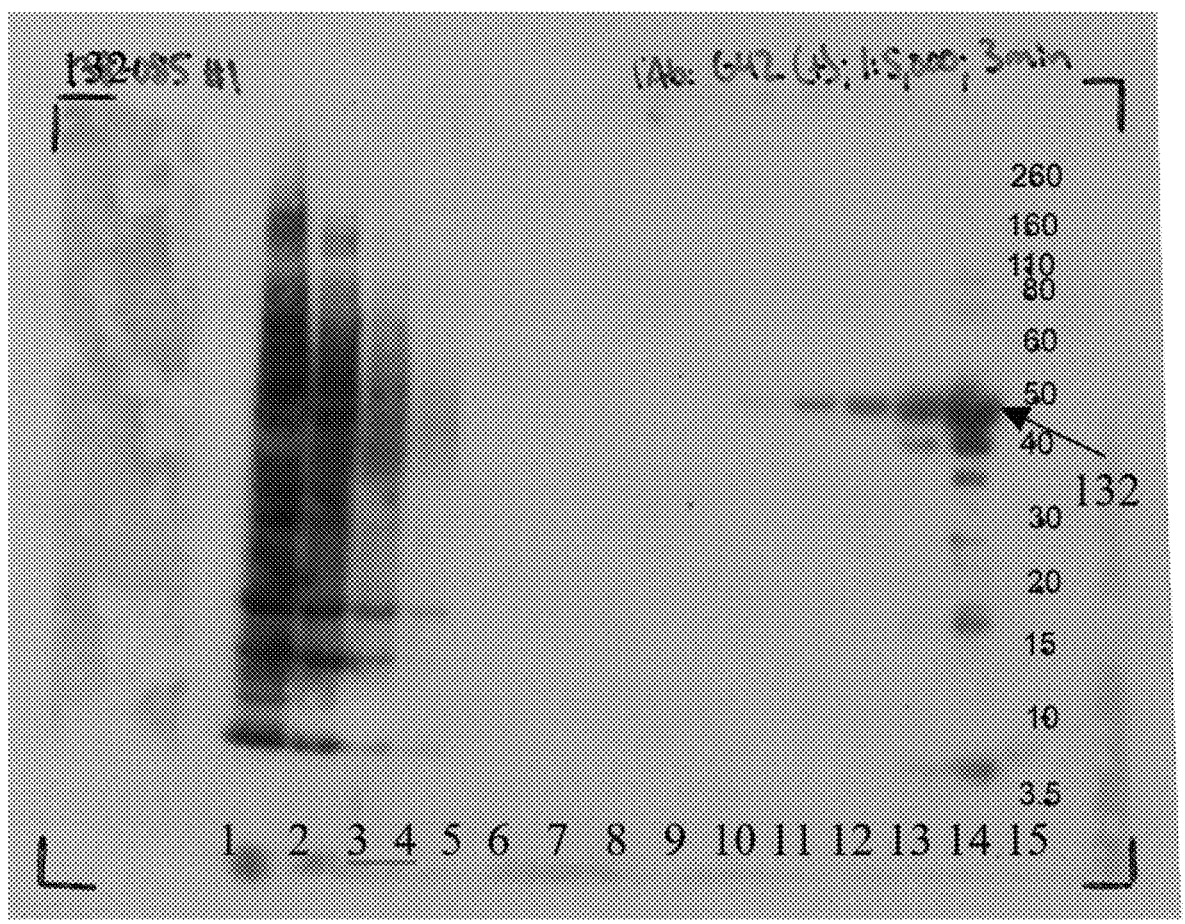
FIG. 7 is an image of immune staining on a Western blot with CWD+sera showing a reaction.
Figure 8:
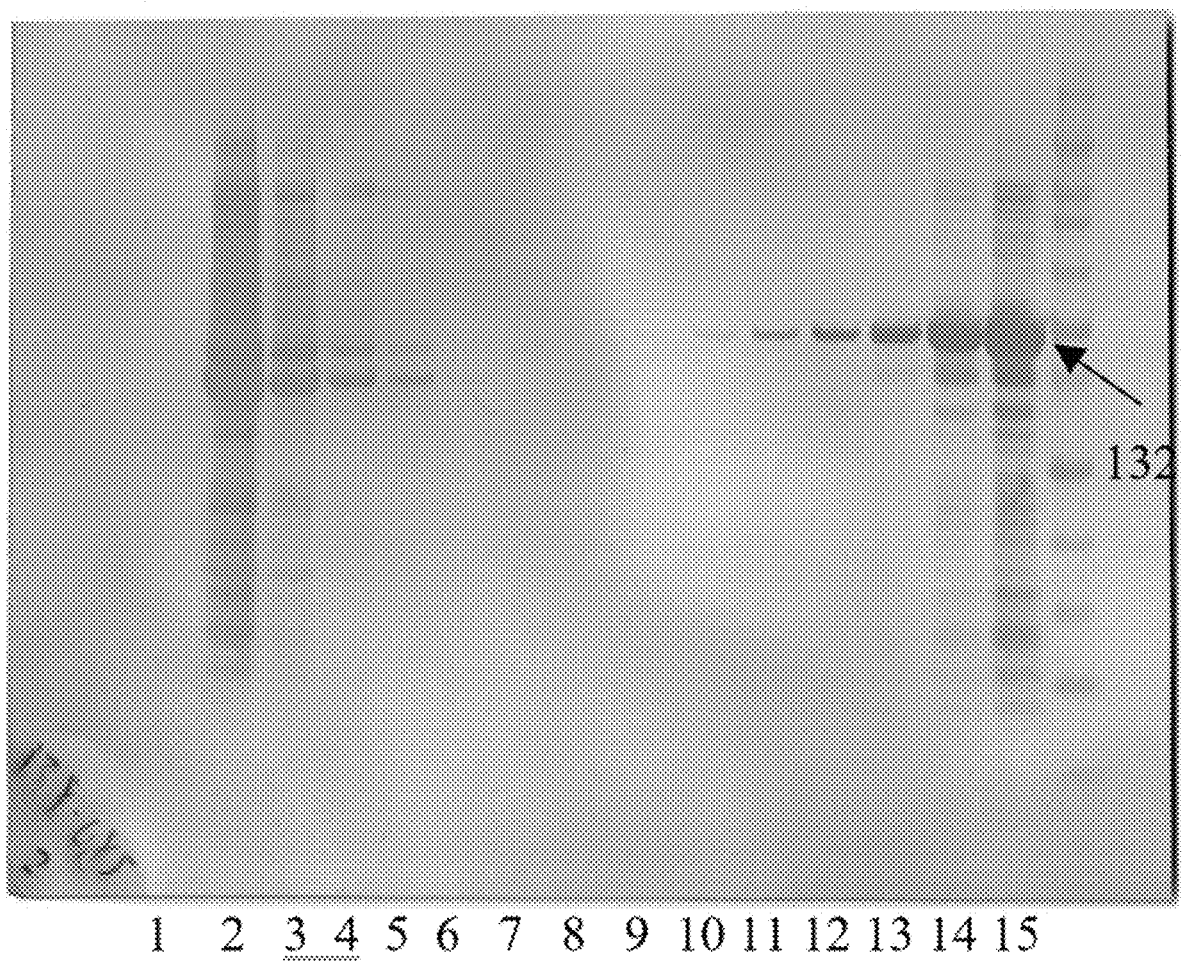
FIG. 8 is a Coomassie blue-stained PVDF membrane containing the novel *Spiroplasma* recombinant protein sample before western blotting with control sera.

Follow-up studies were completed. Specifically, the recombinant protein for the newly discovered surface novel spiralin made from the partial sequence of the newly discovered novel spiralin protein immune reacted with the same CWD positive sera and not with the control sera (FIG. 7 shows reaction; FIG. 8 shows no reaction).

The sequence of the recombinant spiralin protein detected in cultured novel *Spiroplasma* derived from CWD-infected tissue is set forth in the attached sequence listing (SEQ ID 1).

Figure 9:
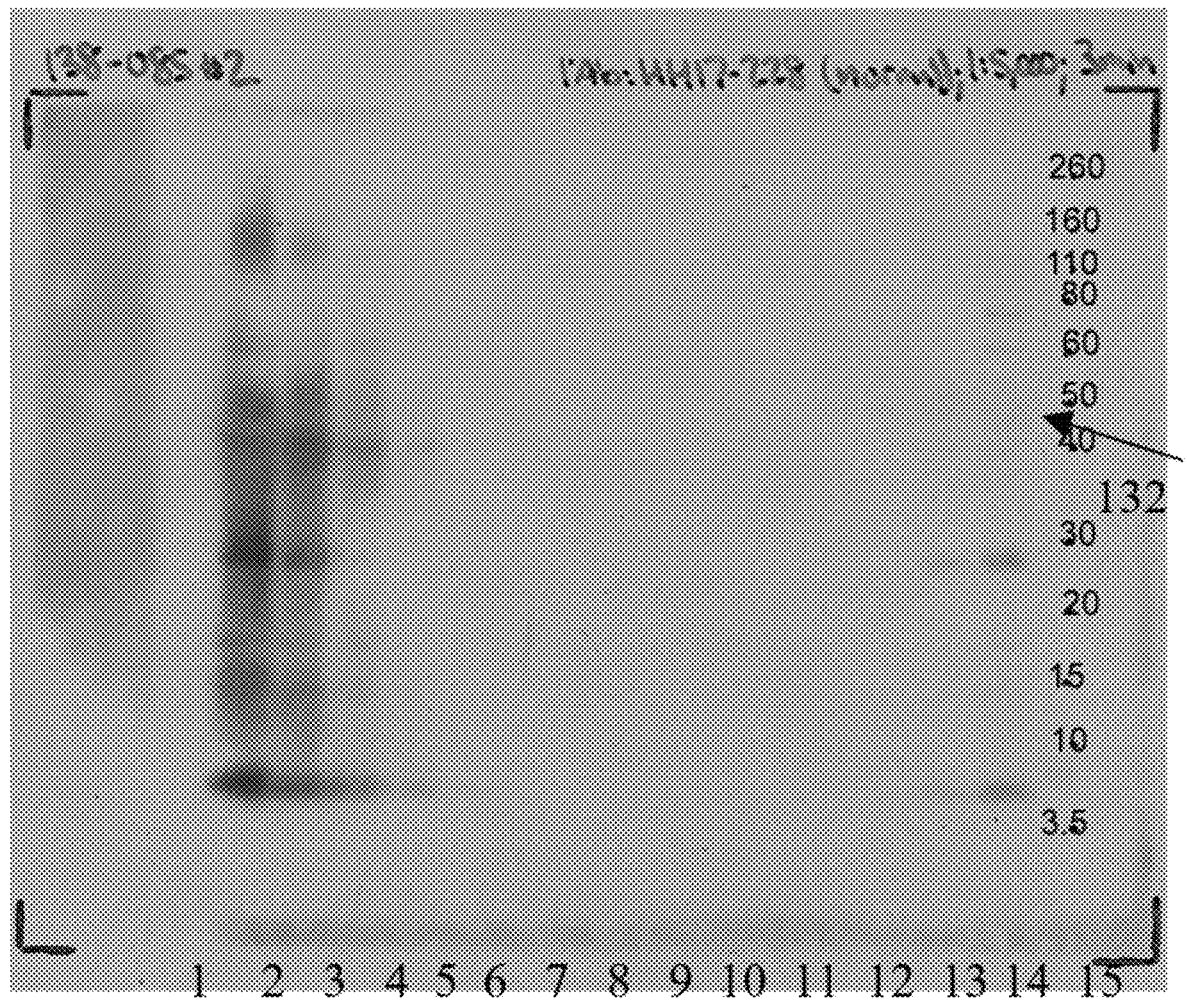
FIG. 9 is an image of immune staining on a Western blot with control sera showing lack of immune reaction.

As seen in FIGS. 7 and 9, the recombinant spiralin protein immune reacted with CWD positive sera and not with the normal sera. FIG. 7 shows immune staining on Western blot with CWD+sera; FIG. 9 shows the lack of an immune reaction on Western blot to control sera.

Figure 6:
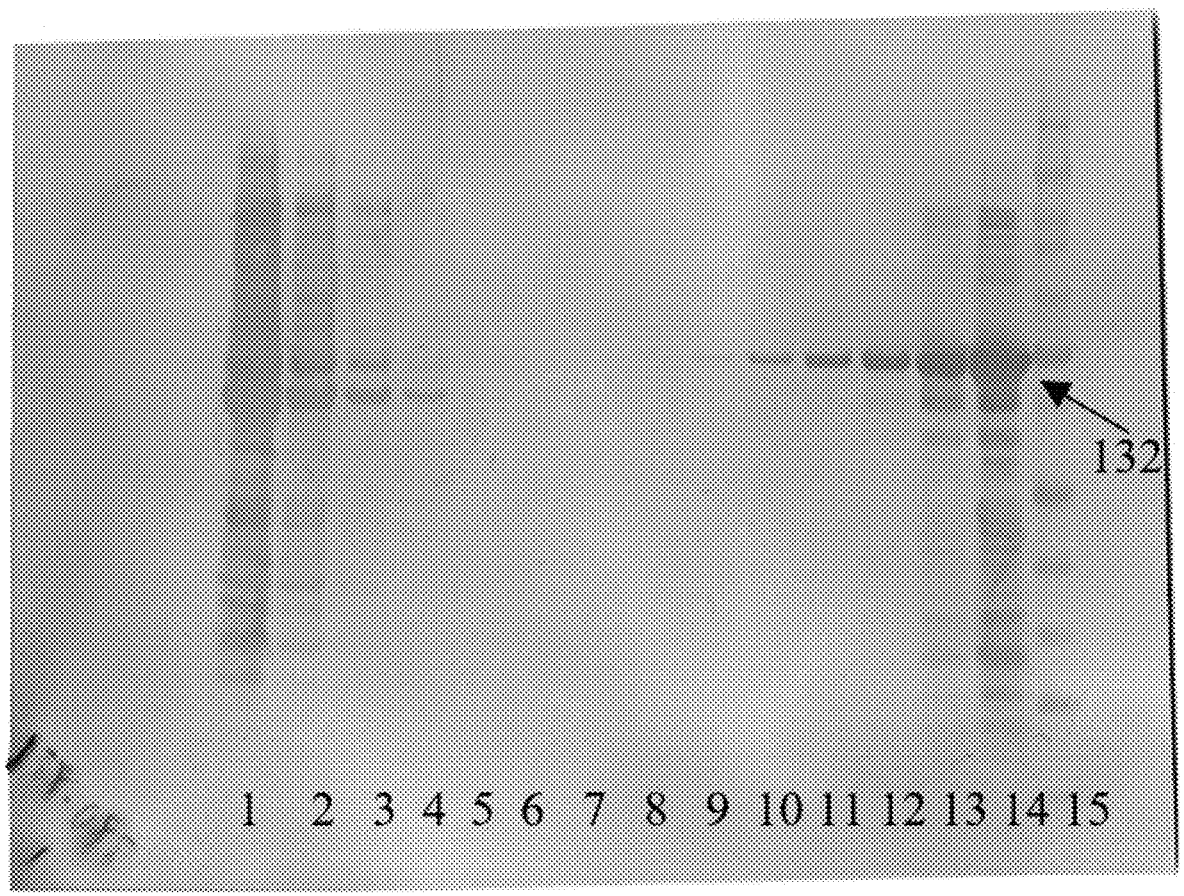
FIG. 6 is a Coomassie blue-stained PVDF membrane containing the novel *Spiroplasma* recombinant protein sample before western blotting with CWD+sera.

FIG. 6 shows a Coomassie blue-stained PVDF membrane containing the novel *Spiroplasma* recombinant protein sample before western blotting with CWD+sera. FIG. 8 shows a Coomassie blue-stained PVDF membrane containing the novel *Spiroplasma* recombinant protein sample before western blotting with control sera.

Specifically, the underlined portion of the aforementioned sequence represents a portion of the unique spiral plasma that reacted with CWD serum.

A preferred embodiment of the ELISA live test as part of this invention is the indirect ELISA wherein the sera sample is antigen-coated on the plate and screened with the recombinant spiralin protein for antigen/antibody reaction. Several secondary antibodies will bind to the primary antibody and the test is highly flexible in that the same secondary antibody may be used for several primary antibodies.

Figure 10:
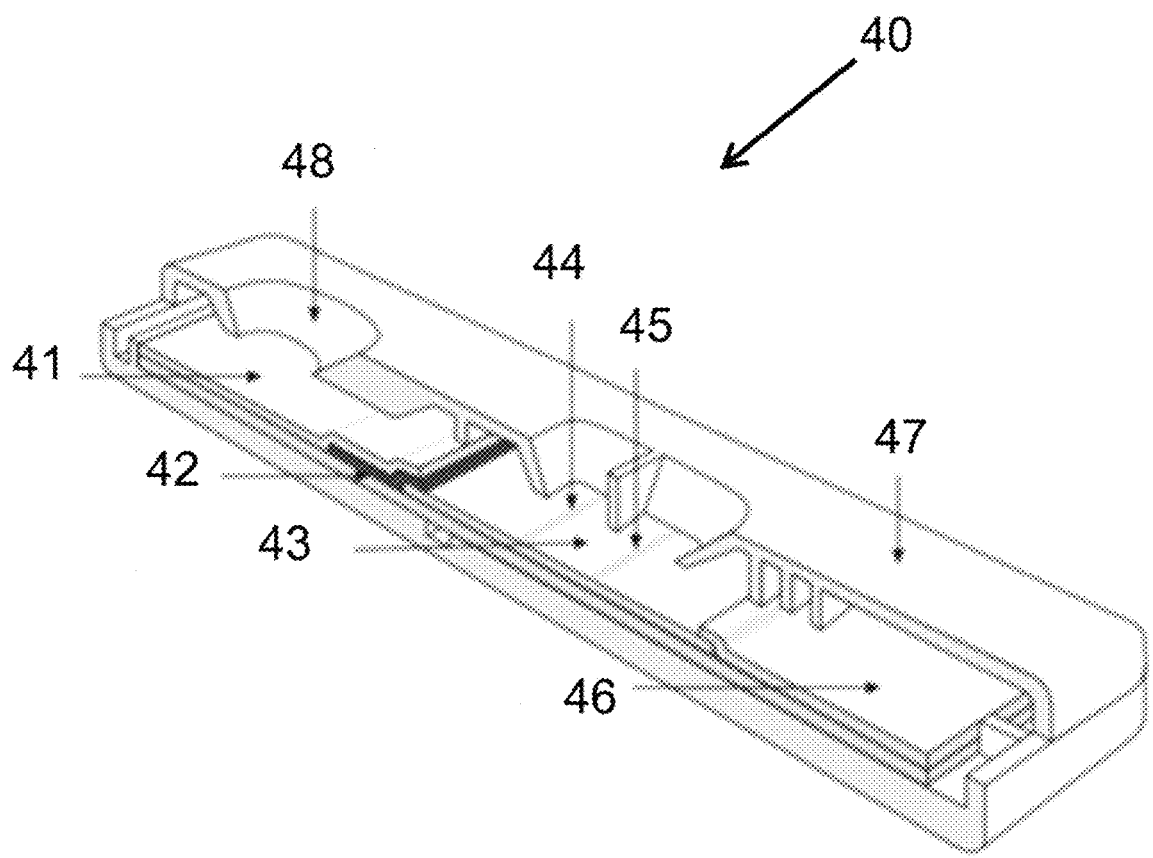
FIG. 10 is an example of a lateral flow test of an embodiment of the apparatus of the present invention.

The present invention also provides for a lateral flow test to detect CWD. An example of such a test is shown in FIG. 10. A lateral flow test (LFT) of the present invention is simple to use and requires no highly technical personnel. It is a one-step, has no wash steps, and preferably displays a result within 5-10 minutes. Such a lateral flow test is portable and thus suitable for field testing. Such a test is highly sensitive and specific. A LFT of the present invention requires only a low sample of volume and little or no samples/reagents preparations. Such LFTs provide for the possibility of multiplexing. Such LFTs are low cost with a high potential for commercialization.

FIG. 10 shows an embodiment of a lateral flow test of the present invention used to detect CWD. As seen in FIG. 10, a partial cutaway of a lateral flow test 40, a sample port 48 is provided for a test sample. A sample pad 41 functions to process sample and control flow onto the conjugate pad 42. The conjugate 41 is a medium for dispensing and drying nanoparticles. Conjugate pad 41 provides controlled release of re-solubilized conjugate onto the nitrocellulose membrane 43. The nitrocellulose membrane 43 provides an ideal solid phase for immobilizing/test line 44 and control line 45 reagents. A wick/absorbent pad 46 provides uniform capillary flow through the membrane, absorbs applied sample and prevents backflow. A housing 47 prevents contamination of the device.

The immune reaction of the CWD positive sera is to the whole recombinant spiralin protein and not necessarily to the small fragment of spiralin derived from the novel spiralin on the membrane surface of the CWD-associated *Spiroplasma* sp. The present inventor will have an ongoing project to identify the complete sequence of the spiralin protein on the surface of the CWD-associated *Spiroplasma* by using real-time PCR METHOD to which new recombinant protein will be made and tested against sera from CWD infected and normal deer.

In certain embodiments of the lateral flow tests of the present invention, *Spiroplasma* heat shock protein will be present to confirm the positive reaction to presence of the microbe in the sample. In other embodiments, the *Spiroplasma* heat shock protein is not needed. Preferably, the spiralin and other surface antigens that presumably will identify specific strains/species of the microbe will be present on the test strip and will be useful in tracing the source of a positive reaction.

PARTS LIST

The following is a list of parts and materials suitable for use in the present invention:
10 cell
11 *Spiroplasma* TSE isolate surface protein/*Spiroplasma* pathogen
12 prion receptor/normal prion isoform receptor protein
13 cell surface
14 *Spiroplasma*-specific heat shock protein/Hsp60
15 *Spiroplasma*-specific glycans
16 test strip
17 backing
18 sample zone
19 conjugation zone
20 membrane
21 absorbent pad
22 sample
23 primary capture agent
24 test band
25 secondary capture agent
26 control band
27 positive result
28 negative result
29 flow direction
30 lateral flow test
41 sample pad
42 conjugate pad
43 membrane
44 test line
45 control line
46 absorbent pad
47 housing
48 sample port
101 arrow
132 arrow identifying protein All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A test apparatus for a live serological test to detect the presence or absence of a transmissible spongiform encephalopathy-associated *Spiroplasma* infection, wherein the test apparatus contains a recombinant protein comprising the amino acid sequence set forth in SEQ ID NO: 1.

2. The live serological test apparatus of claim 1, wherein the live test is a lateral flow test.

3. The lateral flow test of claim 2, wherein the lateral flow test produces a positive result when a TSE-associated *Spiroplasma* infection is detected and a negative result when a TSE-associated *Spiroplasma* infection is not detected.

4. A method for confirming a positive result of the lateral flow test of claim 3, the method comprising the following steps:
   (a) incubating a filtered blood or tissue sample in *Brucella*-type media or agar plates at 35° C. for 6 to 14 days; and
   (b) following the incubation, observing an appearance of the sample to ensure the *Brucella*-type media appears slightly turbid and motile *Spiroplasma* can be readily seen by dark-field microscopy, or the agar plates develop subsurface colonies characteristic of *Spiroplasma* growth.

5. A method for detecting TSE in living humans and other mammals utilizing the lateral flow test of claim 3.

6. The lateral flow test of claim 3, wherein the lateral flow test comprises:
   a sample port;
   a sample pad;
   a conjugate pad;
   a nitrocellulose membrane;
   a test line;
   a control line;
   a wick/absorbent pad; and
   a housing.

7. A method for detecting TSE in a living mammal utilizing the lateral flow test of claim 6, wherein:
   the sample port receives a test sample obtained from the living mammal, the control line indicates whether the sample was properly received, and the test line indicates whether or not the sample contains TSE.

8. The method of claim 7, wherein the test sample is a tissue and/or body fluid sample.

9. The method of claim 8, wherein the test sample is selected from the group consisting of brain tissue, spinal cord, dura mater, corneal tissue, lymph node tissue, tonsil tissue, rectal tissue, feces, urine, cerebrospinal fluid, aqueous fluid from an eye, vitreous fluid from an eye, spermatozoa, semen, milk, and blood.

10. The method of claim 8, wherein the living mammal is a sheep, goat, deer, elk, camel, feline animal, or cattle.

11. The method of claim 10, wherein the result occurs in less than 1 hour.

12. The method of claim 10, wherein the result is displayed within 5-10 minutes.

13. The method of claim 8, wherein the body fluid comprises urine, cerebrospinal fluid, aqueous fluid from an eye, vitreous fluid from an eye, spermatozoa, semen, milk, or blood.

14. A method for confirming that a mammal does not have TSE, the method comprising testing the mammal utilizing the lateral flow test of claim 6.

\* \* \* \* \*

SEQUENCE LISTING

```
Sequence total quantity: 1
SEQ ID NO: 1           moltype = AA   length = 379
FEATURE                Location/Qualifiers
source                 1..379
                       mol_type = protein
                       organism = synthetic construct
SEQUENCE: 1
MSNDKKREVE  SFYNHDGTFF  GHPNQPDRKA  QEGEVKQQHQ  EKPAQEPKKP  TFFTGLSEVI   60
SPLYGKKAKE  PNQRDAVGYD  QVAKTEINLA  SSSIQKIINE  QVDEKKNNFV  KPSNQSPKQL  120
DDQVDNLVKI  KLSENLRESN  ITPAVKNNDQ  KFYRSNKLSE  QAAKTESFLF  RPRKNGENIF  180
GERTAELTLE  LENIKEKIRN  TNPRSNFSSN  YEQTAMFGGI  EEQKEINRQI  QDAINNVYQV  240
EDDFSEDMPL  SDRRKKIESN  SIHASSMRLQ  KIKNLQNLNL  QDQFLRRPKT  ISQSSLDYHK  300
MLQKLRDKNP  DEESRKVSKY  YANNNPYLER  MIKLEEENFE  QANNSRKERI  HEEASQVKDN  360
NSNKNRSGGG  SHHHHHHHH                                                  379
```